United States Patent [19]

LeBlanc, Jr. et al.

[11] 4,120,292
[45] Oct. 17, 1978

[54] IMPLANTABLE ELECTROCHEMICAL SENSOR HAVING AN EXTERNAL REFERENCE ELECTRODE

[75] Inventors: Oliver H. LeBlanc, Jr.; Leonard W. Niedrach; William H. Stoddard, Jr., all of Schenectady, N.Y.

[73] Assignee: General Electric Company, Schenectady, N.Y.

[21] Appl. No.: 759,468

[22] Filed: Jan. 14, 1977

Related U.S. Application Data

[63] Continuation of Ser. No. 620,707, Oct. 8, 1975, abandoned.

[51] Int. Cl.² ............................................. A61B 5/00
[52] U.S. Cl. .................................. 128/2 E; 128/2.1 F; 204/195 B
[58] Field of Search .................... 128/2 E, 2.1 E; 204/195 B, 195 R, 195 F, 1 H

[56] References Cited

U.S. PATENT DOCUMENTS

| | | | |
|---|---|---|---|
| 2,168,867 | 8/1939 | George | 204/195 F X |
| 3,077,446 | 2/1963 | Berg | 204/195 F |
| 3,151,052 | 9/1964 | Arthur et al. | 204/195 F |
| 3,224,433 | 12/1965 | Dalebor | 128/2 E |
| 3,224,436 | 12/1965 | Massena | 128/2.1 E |
| 3,249,103 | 5/1966 | Woodhouse | 128/2.1 E |
| 3,605,722 | 9/1971 | Riseman et al. | 128/2.1 E |
| 3,705,089 | 12/1972 | Grubb | 204/195 F |
| 3,718,569 | 2/1973 | Petersen et al. | 204/1 H X |
| 3,823,706 | 7/1974 | Davis | 128/2.1 E X |
| 3,869,354 | 3/1975 | Montelvo, Jr. | 204/195 B X |
| 3,878,830 | 4/1975 | Bicher | 128/2 E |

OTHER PUBLICATIONS

Reeves et al., "O₂ Tension ... Significance", Federation Proceedings, vol. 16, pp. 693–696, Sep. 1957.
Joseph, "Heterogeneous ... Protein Solutions", J. Biol. Chemistry, pp. 389–405, 1938.

*Primary Examiner*—Robert W. Michell
*Assistant Examiner*—Lee S. Cohen
*Attorney, Agent, or Firm*—Charles T. Watts; Joseph T. Cohen; Marvin Snyder

[57] ABSTRACT

The reference electrode, which is physically removed from the sensing electrode, is functionally connected by means of a Ringer's solution formulation serving as an electrolyte bridge between the reference electrode and the fluid or tissue of the patient under test.

2 Claims, 2 Drawing Figures

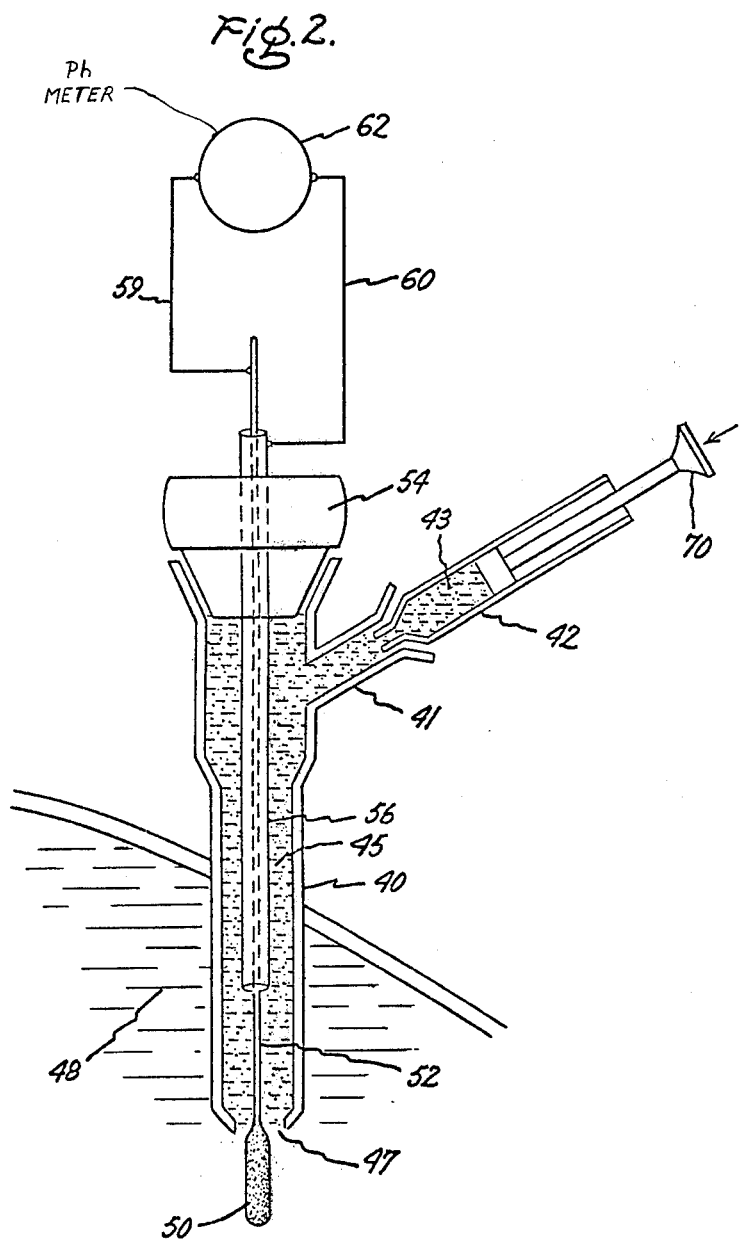

IMPLANTABLE ELECTROCHEMICAL SENSOR HAVING AN EXTERNAL REFERENCE ELECTRODE

This is a continuation, of application Ser. No. 620,707, filed Oct. 8, 1975, now abandoned.

The present invention relates generally to the art of measuring or monitoring ion activity in vital fluids and tissues, and is more particularly concerned with a novel implantable specific ion sensor assembly having special utility in in vivo monitoring applications.

BACKGROUND OF THE INVENTION

An electrochemical sensor consists of a paired sensing and reference electrode combination. In measuring pH or other ion activity it is necessary to use an ion sensing electrode in conjunction with the reference electrode which also makes contact with the system on which measurements are being made. In certain cases the reference electrode can make direct contact with the system which necessitates that the system contain a fixed and known concentration of an ion that can enter into equilibrium with the reference electrode. More generally, the reference electrode is immersed in a solution having a known content of the ion with which it equilibrates and contact of this solution with the system being measured is made via a suitable "salt bridge." This bridge may consist of an extension of the vessel in which contact with the reference electrode is made. A specific ion sensor of the latter type is disclosed and claimed in U.S. Pat. application Ser. No. 491,772, filed July 24, 1974 (now abandoned), and assigned to the assignee hereof.

SUMMARY OF THE INVENTION

By virtue of our novel concepts to be described, new and important advantages of economy and utility can be obtained. In particular, the electrochemical sensor of this invention avoids the necessity for various structural components essential to prior devices of this general type and yet all the essential functions are retained. In addition, the necessity for removing blood or other samples from the patient's body for test purposes can be avoided, the reference electrode need not be introduced into the patient and it need not be biocompatible. Moreover, these advantages can be obtained without incurring any performance or reliability penalty and without increasing production cost.

Our basic concept is to make multiple use of an injectable isotonic solution. Thus, a solution of a kind normally introduced intravenously serves as an electrolyte in equilibrium with the reference electrodes and as an electrolyte bridging between the blood, for example, and the reference electrode. The performance of the sensing electrode is not impaired since in accordance with this invention the solution is introduced into the bloodstream at a location slightly downstream from the active tip of the sensing electrode. Similarly, in the case of tissue ion activity measurement, a suitable isotonic solution is employed as the reference electrode electrolyte and as the bridge but is stationary instead of continuously flowing as in the case above because muscle or other tissue outside the vascular compartment only slowly absorbs injected fluids. Again, though, the active tip of the sensing electrode is disposed out of contact with the isotonic solution electrolyte although the insulated lead and that electrolyte solution share the catheter lumen. In both cases, however, the reference electrode is directly in contact with the isotonic solution electrolyte within the catheter or within a conduit communicating therewith for delivery of the isotonic solution into the catheter lumen continuously or intermittently, as required.

As indicated above, we have discovered that the essential reference electrode function can be adequately performed while isolating the reference electrode and its electrolyte from the body fluid or tissue being tested. A suitable reference electrode/electrolyte combination is a chlorided silver wire, tube or other configuration in contact with a saline solution. We have also found that the particular nature or composition of the isotonic saline solution is generally not critical to the reference electrode function, the various saline or Ringer's solution formulations, for example, adequately serving the purpose for proper reference electrode function. Still further, for some monitoring and measurement purposes not requiring continuous reference electrode function, the isotonic solution flow can be controlled and interrupted as required for the other purposes without significant penalty to the reference electrode function.

On the basis of these discoveries, it will be understood that the assembly of this invention, briefly described, includes an insulated sensing electrode with an electrochemically active portion at one end, cannula means receiving and enclosing a portion of the insulated length of the sensing electrode, and electrolyte delivery means including a conduit communicating with the cannula means and an electrolyte source, all in combination with a metallic reference electrode positioned in the assembly at a location removed from the electrochemically active portion of the sensing electrode and exposed to direct contact with electrolyte delivered through the conduit into the cannula means.

As will be described in detail, the reference electrolyte is in liquid form and, preferably, the reference electrode is located in the conduit rather than in the cannula. Additionally, the cannula is suitably in the form of a catheter for insertion into a blood vessel or into muscle tissue or other tissue outside the vascular compartment, and the reference electrode may take the form of a tube extending lengthwise of the catheter and disposed coaxially with the elongated electrode lead. In these various design alternatives, it is generally desirable that the insertable components be miniaturized so far as possible, but it should be recognized that it is a special advantage of this invention that the reference electrode may be comparatively large and therefore of simple design.

In view of the foregoing description, those skilled in the art will further understand that the reference electrode half cell of this new sensor is itself a new departure from the prior art constituting a novel subcombination of the specific ion sensor of this invention. Thus, this half cell comprises a tubular body of electrically insulating material having an open end for communication with a subject to be tested, an elongated silver reference electrode in the tubular body and extending therefrom for connection to electrical readout means, and an isotonic solution electrolyte in contact with the reference electrode and the open end of the tubular body. Preferably, the electrode is of silver and a portion thereof within the tubular body is coated with silver chloride. Additionally, the electrolyte is a liquid and the tubular body has an inlet opening to receive the electrolyte which flows through the tubular body in contact with the silver chloride coating and out through the open end of the said body.

DESCRIPTION OF THE DRAWINGS

Those skilled in the art will gain a further and better understanding of this invention on consideration of the detailed description set forth below taken in conjunction with the drawings accompanying and forming a part of this specification, in which.

DETAILED DESCRIPTION OF THE INVENTION

Figure 1:
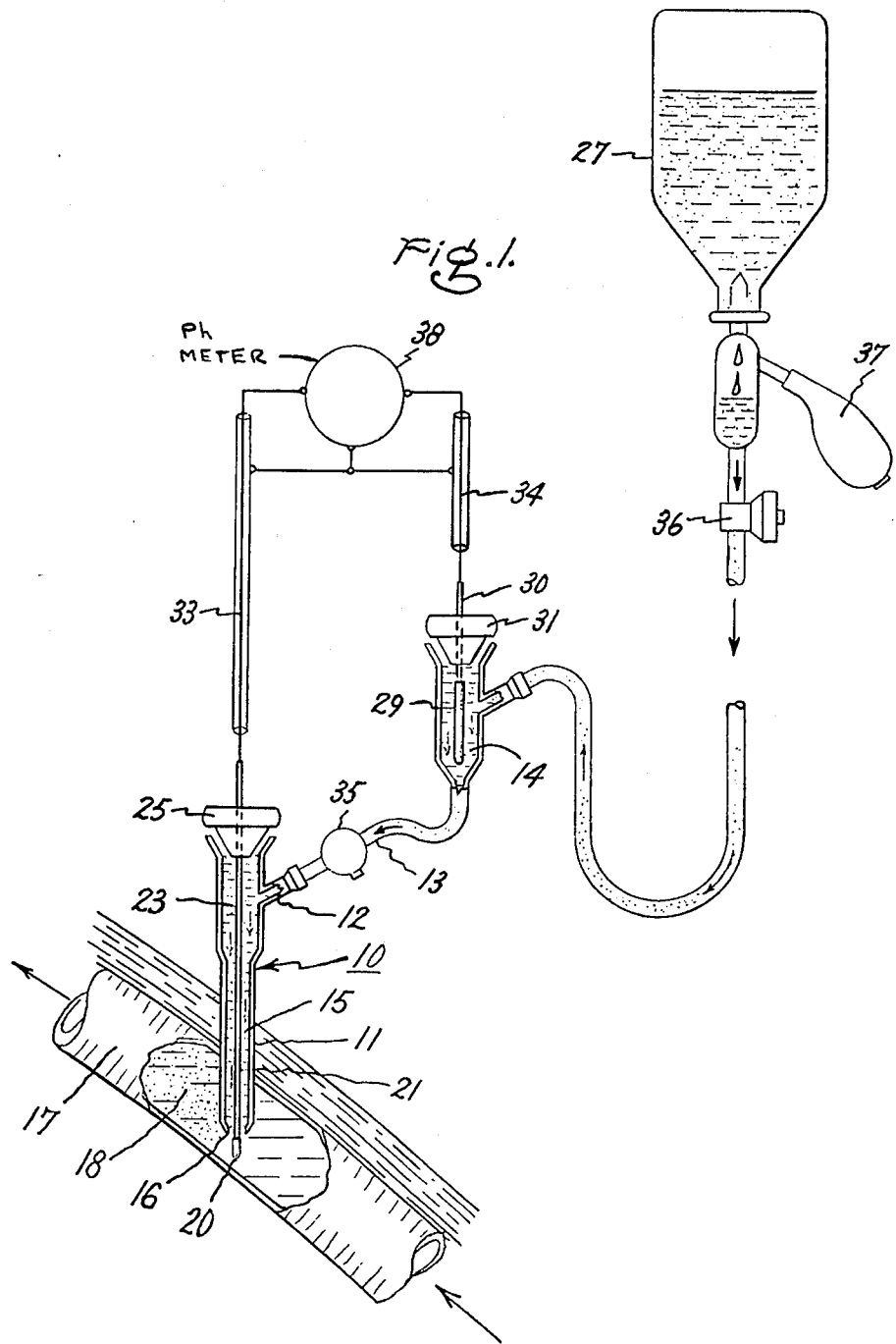
FIG. 1 is a diagrammatic view, partly in section, of a sensor assembly embodying this invention in preferred form, the sensing electrode being implanted in working position in a blood vessel and the reference electrode being disposed in a conduit communicating with an isotonic solution electrolyte reservoir; and, FIG. 2 is a view similar to that of FIG. 1 showing another sensor assembly of this invention in working position with the sensing electrode implanted in muscle tissue and the reference electrode in contact with isotonic electrolyte in gel form.

As illustrated in FIG. 1, in vivo specific ion sensor assembly 10 includes a cannula or catheter 11 having a side arm 12 to receive tubular body or conduit 13 of suitable electrically insulating material through which isotonic solution electrolyte 14 can be introduced into lumen 15 of the catheter. Leading end 16 of the catheter is open and disposed in blood vessel 17 for discharge of electrolyte 14 continuously or intermittently into bloodstream 18 at a point slightly downstream from active tip 20 of sensing electrode 21 which is suitably the same in construction and mode of operation as that disclosed and claimed in copending patent application Ser. No. 491,772 referred to above. Insulated lead 23 of sensing electrode 21 extends through lumen 15 and through cap 25 fluid-tightly closing the other end of catheter 11. Conduit 13 communicates with isotonic solution electrolyte reservoir 27 and at a point between the reservoir and catheter 11, reference electrode 29 in the form of a silver wire bearing a silver chloride coating is disposed in the conduit, lead 30 of the electrode extending through cap 31 fluid-tightly sealing the reference electrode access opening in the conduit. Shielded cables 33 and 34 connect leads 23 and 30 of the sensing and reference electrodes, respectively to pH meter 38.

In operation of the FIG. 1 assembly, flow of electrolyte through conduit 13 is regulated by three-way stop cock 35 and valve 36 disposed downstream and upstream, respectively, from reference electrode 29, and by pump 37 of the venoclysis set. Thus, as indicated above, readings may be taken continuously or intermittently and meter 38 may be coupled to a recorder if desired. It will be understood that during periods of such use the isotonic solution serves as an electrolyte bridge between bloodstream 18 and reference electrode 29 and also in establishing the reference electrode/electrolyte couple. Stop cock 35 is open at such times and the electrolyte is therefore in contact with both the bloodstream and reference electrode 29.

The specific ion sensor assembly of FIG. 2 likewise includes a catheter 40 having a side arm 41 to receive a tubular body or conduit 42 of suitable electrically insulating material through which gelled electrolyte 43 can be introduced into the catheter to fill lumen 45 thereof. The catheter also has an open end 47 disposed in muscle tissue as indicated at 48. Active tip 50 of the sensing electrode extends through the open end 47 of the catheter into muscle tissue 48 while the lead 52 of the electrode extends the length of catheter lumen 45 and through cap 54, fluid-tightly closing the opposite end of the catheter.

Reference electrode 56 in the form of a chlorided silver tube likewise extends through cap 54 and through a portion of the length of lumen 45 of the catheter in which it is coaxially disposed around lead 52 of the reference electrode. Electrode 56, however, terminates within the catheter at some distance removed from tip 50 and does not directly contact tissue 48.

Electric cables 59 and 60, preferably of the shielded type described in the reference of FIG. 1, connect the sensing and reference electrodes, respectively, to pH meter 62.

The specific ion sensor assembly of FIG. 2 operates generally as described in reference to FIG. 1, the basic difference being that a gelled or stationary electrolyte is used instead of a flowing electrolyte isotonic solution. This is because of the physical difference between the bloodstream and muscle tissue, particularly in respect to absorption rate. The development of vacancies or bubbles within the catheter 40 can lead to erroneous pH readings. Accordingly, a syringe 70 is provided for maintaining a void-free condition within lumen 45.

If desired, one may in accordance with this invention use two separate catheters and separate the sensing electrode from the reference electrode in that manner without impairing the operation of either one. Catheters of generally the FIG. 2 type would be specially suited for this purpose and would find use in applications involving muscle tissue and the like rather than in the vascular compartment, where multiple openings are not desirable.

While the illustrated apparatus has been described with particular reference to hydrogen ion activity measurement or monitoring operations, those skilled in the art will understand that this invention is equally applicable to the monitoring or measurement of other ions in the blood or in muscle tissue or in other fluids or tissues of the body. In other words, the basic new principles of design and mode of operation of the sensors of this invention apply as well to other specific ion in vivo sensing systems and devices incorporating the sensing electrode and reference electrode combination.

The following are illustrative, but not limiting, examples of the practice of our present invention:

EXAMPLE I

An in vivo blood pH sensor assembly like that illustrated in FIG. 1 was used in tests on a dog. The pH-sensing electrode was a polymer membrane pH sensor as described and claimed in U.S. Pat. No. 3,743,588 assigned to the assignee hereof. This sensor was inserted through a cannula implanted in the left carotid artery, the cannula being continuously flushed with lactated Ringer's solution (130 mEq sodium ion, 4 mEq potassium ion, 3 mEq chloride ion, 28 mEq lactate ion) supplied under pressure from the venocylsis set shown in FIG. 1. The flow rate of the electrolyte was approximately 1 milliliter per minute. The reference electrode in this instance was a chlorided silver wire sealed into one end of a small diameter plastic tube which was filled with a solution of 4N potassium chloride that was gelled with two weight percent Agar-Agar. The potassium chloride electrolyte furnished the chloride ion concentration to establish the electrochemical potential of the silver/silver chloride couple, and it also served as an intermediate electrolyte bridge between the chlorided silver wire and the lactated Ringer's solution with which it was in contact at the opposite end of the plastic tube. The electrodes were connected as described above to the pH meter (Instrumentation Laboratories Model 245), the output being displayed on a recorder (Hewlett-Packard Model 7100B). Electrical pick-up noise was reduced to less than 1 millivolt by effective shielding of the cables. The potential difference between the pH-sensing electrode and the reference electrode was precalibrated in vitro in buffers thermostated at 37° C. before implantation in the animal, and this pH calibration was used throughout the in vivo test. The in vivo test lasted approximately 5½ hours, during which time arterial pH, as measured by the in vivo sensor, was continuously displayed. To monitor the accuracy of these data, blood samples were withdrawn from the site of the pH sensor, through the three-way stopcock attached to the exterior end of the cannula, and their pH independently determined in vitro using a blood gas and pH analyzer (Radiometer Model 27GM). Eight such samples were taken at intervals of approximately 45 minutes during the 5½ hour test, and the difference between the in vitro measurement and the in vivo sensor reading at the time of sampling were compared. In three instances this difference was +0.03 pH units, in one instance +0.01 pH units, and in four instances there was no difference. On the average, then, in this test the in vivo sensor indicated a blood pH higher by 0.01 pH unit than that indicated by the in vitro method, with a root mean square difference of 0.02 pH units. The accuracy of the in vivo measurements was also verified after the test by repeating the in vitro calibration or the potential difference between the pH-sensing electrode and the reference electrode in buffers thermostated at 37° C. The calibration was found to have changed by +0.02 pH units during the course of the 5½ hour test. The two methods of judging the accuracy of the in vivo pH measurements were thus in reasonable agreement, and the accuracy found by either method was satisfactory.

EXAMPLE II

An in vivo muscle pH assembly like that illustrated in FIG. 2 was used in tests on a dog. A catheter was first implanted percutaneously into muscle tissue on the outer aspect of the upper thigh, then the assembly consisting of the pH-sensing electrode and the silver—silver chloride reference electrode inserted as shown into this catheter. The tip of the pH-sensing electrode extended into the muscle tissue approximately 1 centimeter beyond the end of the catheter. An electrolyte solution of isotonic 0.15 molar NaCl gelled by the addition of 3 weight percent methylcellulose (Dow 90 HG Premium Grade Methocel) was then injected by syringe into the side arm of the catheter, filling its volume of approximately 0.4 milliliters and making contact with the muscle tissue at the tip of the catheter. The syringe was then removed and the side arm closed with a fluid-tight cap (not shown). The electrodes were connected as in Example I to a pH meter and recorder to yield a continuous record over the 3-hour test. The potential difference between the pH-sensing electrode and the silver—silver chloride electrode was precalibrated in vitro at 37° C. in buffers containing 150 mEq chloride ion. In the case of muscle pH monitoring, unlike that for blood pH monitoring, there is no alternative, in vitro method for quantitatively determining the accuracy of the pH values indicated by the in vivo sensor. Therefore, only a repeat of the calibration procedure at the termination of the in vivo test could be used; it was found that the calibration had changed by −0.01 pH units during the 2-hour test. Furthermore, the muscle pH data obtained during the test appeared to be reasonable as compared to the experience obtained by other investigators, in that muscle pH was generally about 0.1 pH unit lower than arterial blood pH under most conditions, an increase or decrease in one paralleling that in the other. An exception was when peripheral vasoconstriction was induced by a severe hemorrhagic shock, in which case muscle pH fell rapidly to a value about 1 pH unit below arterial pH.

Modifications contemplated in the devices of this invention include thermostating of the reference electrode so that variations in temperature will not affect its potential. This would only be desirable if a very high degree of pH accuracy is required. Secondly, as stated in Example II, instead of having the reference electrode in direct contact with flowing electrolyte solution as shown in FIG. 1, an intermediate salt bridge such as saturated potassium chloride might be provided. The advantage would be that the reference electrode potential would then be independent of the precise composition of the flowing electrolyte and it would be unnecessary to recalibrate the sensor output if flowing electrolyte of different composition were used at some stage of the test.

What we claim as new and desire to secure by Letters Patent of the United States is:

1. A specific ion sensor assembly for in vivo use comprising an insulated sensing electrode having an electrochemically active portion at one end, a catheter receiving coaxially and enclosing a portion of the insulated length of the sensing electrode and having an open end through which the electrochemically active portion of the sensing electrode extends exteriorly of the catheter for contact with a substance of a living organism to be tested, the catheter also having a laterally extending branch, means for delivering electrolyte into the catheter in proximity to the electrochemically active portion including a conduit connected to the catheter branch and communicating with the catheter through said branch for delivery of electrolyte into the catheter from an electrolyte reservoir, a chlorided silver reference electrode positioned in the conduit at a point removed from the catheter branch and exposed for direct contact with electrolyte flowing through the conduit and into the catheter and through the open end of the catheter, an electrolyte consisting essentially of an injectable isotonic solution flowing in the conduit in contact with the reference electrode and into the catheter branch and out of the catheter, and electrical conductor means for connecting the sensing electrode and the reference electrode to electrical readout means including a sensing electrode lead and a reference electrode lead.

2. The sensor assembly of claim 1 in which the electrolyte is a Ringer's solution and valve means is provided in the conduit between the reference electrode and the catheter to control flow of the Ringer's solution into the catheter.

* * * * *